(12) United States Patent
Bergström et al.

(10) Patent No.: US 6,358,050 B1
(45) Date of Patent: Mar. 19, 2002

(54) DENTAL IMPLANT SYSTEMS

(75) Inventors: Nils Gustaf Bergström, Vagnhärad (SE); Niklas Lidskog, Lexington, MA (US)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/171,956

(22) PCT Filed: Aug. 18, 1998

(86) PCT No.: PCT/SE98/01481

§ 371 Date: Oct. 29, 1998

§ 102(e) Date: Oct. 29, 1998

(87) PCT Pub. No.: WO99/08620

PCT Pub. Date: Feb. 25, 1999

(30) Foreign Application Priority Data

Aug. 19, 1997 (SE) ................................................ 9702981

(51) Int. Cl.[7] .................................................. A61C 8/00
(52) U.S. Cl. ........................................................ 433/173
(58) Field of Search ................................. 433/173, 174

(56) References Cited

U.S. PATENT DOCUMENTS

| | | | | |
|---|---|---|---|---|
| 5,040,983 A | * | 8/1991 | Binon | 433/174 |
| 5,281,140 A | * | 1/1994 | Niznick | 433/173 |
| 5,344,457 A | * | 9/1994 | Pilliar et al. | 433/174 |
| 5,439,380 A | * | 8/1995 | Marlin | 433/173 |
| 5,480,304 A | * | 1/1996 | Nardi | 433/173 |
| 5,564,924 A | * | 10/1996 | Kwan | 433/173 |
| 5,733,124 A | * | 3/1998 | Kwan | 433/173 |

FOREIGN PATENT DOCUMENTS

| | | |
|---|---|---|
| EP | 0419431 | 3/1991 |
| WO | 8502337 | 6/1995 |
| WO | 9714372 | 4/1997 |

* cited by examiner

*Primary Examiner*—Todd E. Manahan
(74) *Attorney, Agent, or Firm*—White & Case LLP

(57) ABSTRACT

Dental implant system converter structure (11; 111; 211; 311; 411; 511; 611; 711) for enabling a fixture (1) of a first dental implant system having a trailing end in which a tapered recess (6) opens to support components of a second incompatible dental implant system, the converter structure having a leading end which presents a projection having a tapered profile (15; 115; 215; 315; 415; 515; 615; 715) for seating in the tapered recess in the trailing end of the fixture and a trailing end which presents a profile (18, 20: 108; 208; 308; 408; 508; 608; 708) adapted to enable one or more components (21) of the second dental implant system to be cared thereon. A hybrid dental prosthesis may therefore be formed.

37 Claims, 9 Drawing Sheets

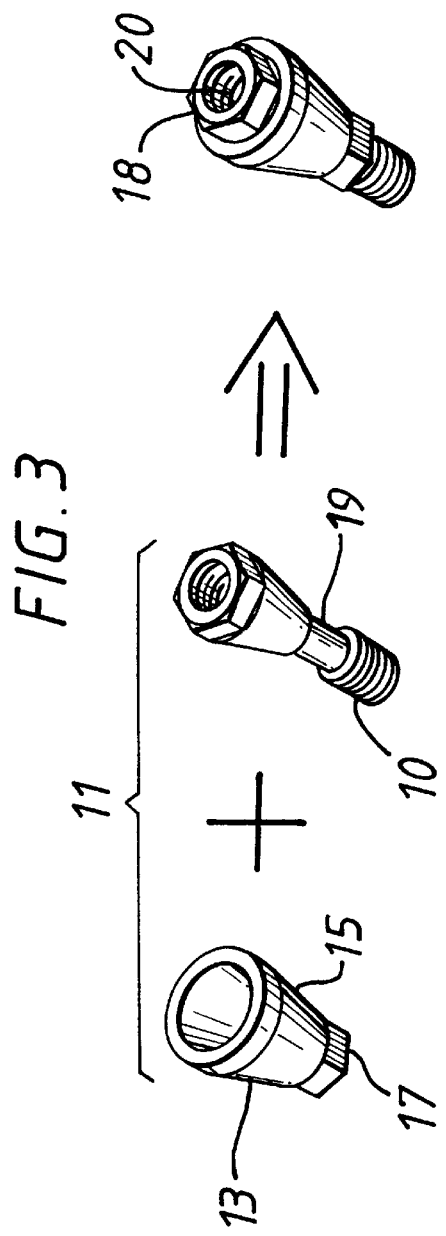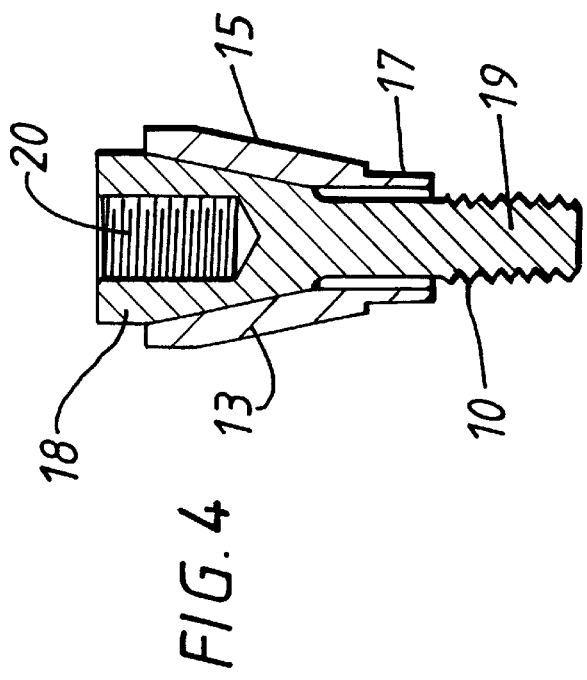

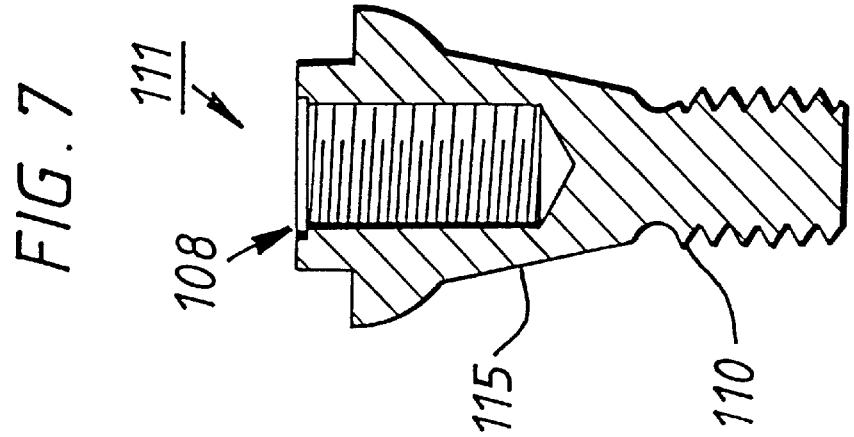
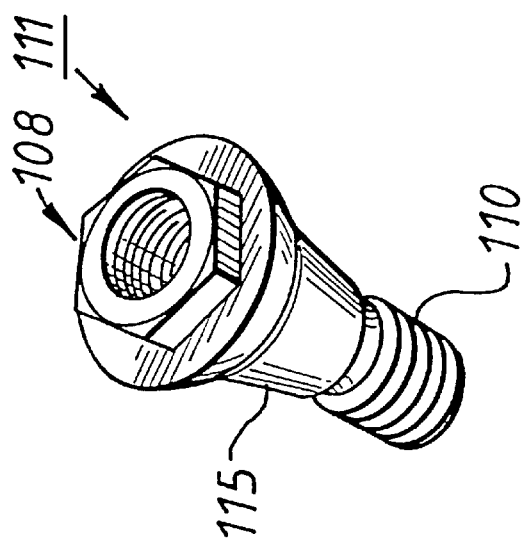
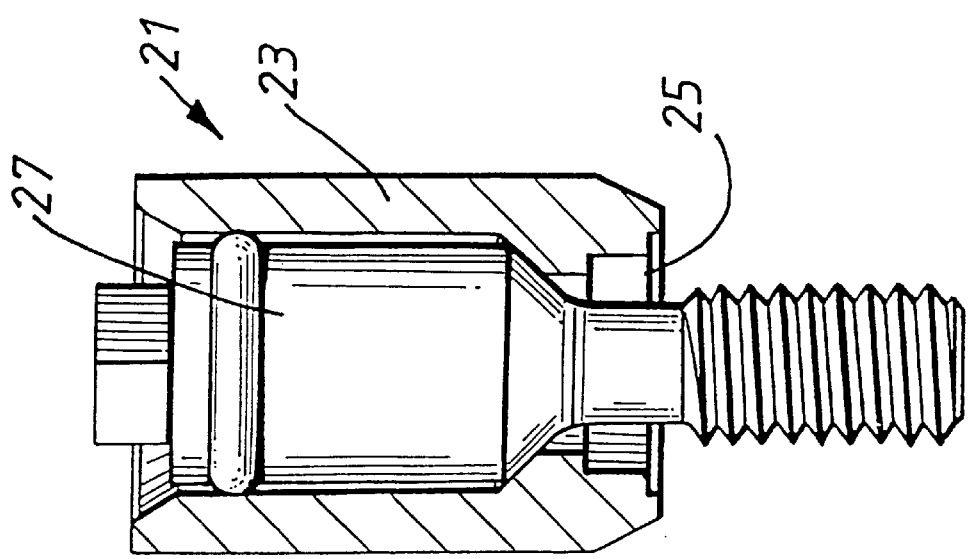
*(Prior Art)*

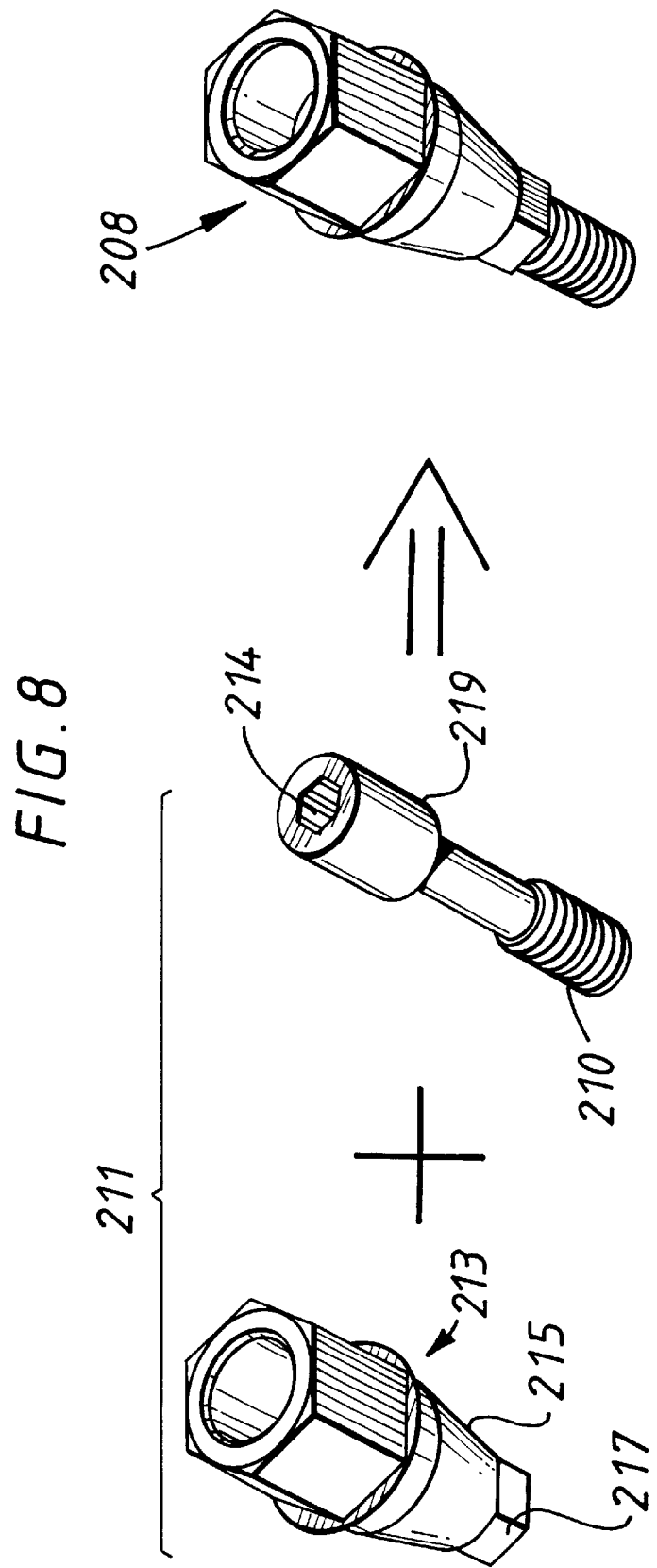

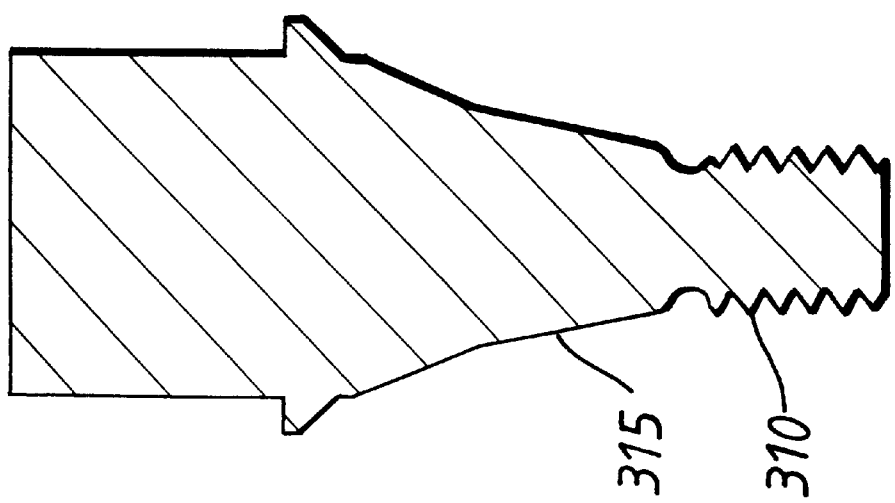
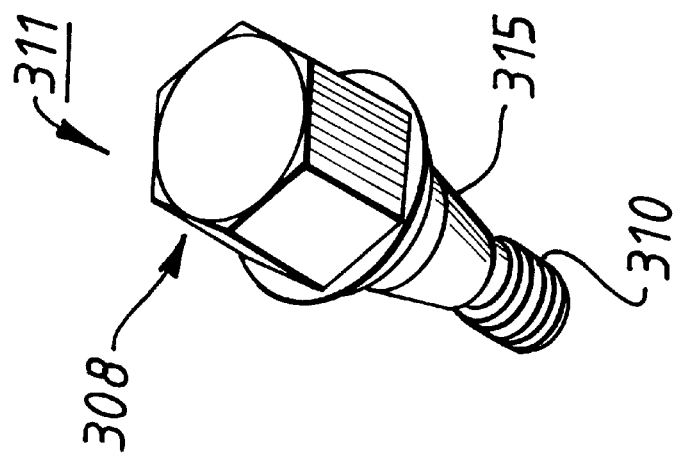
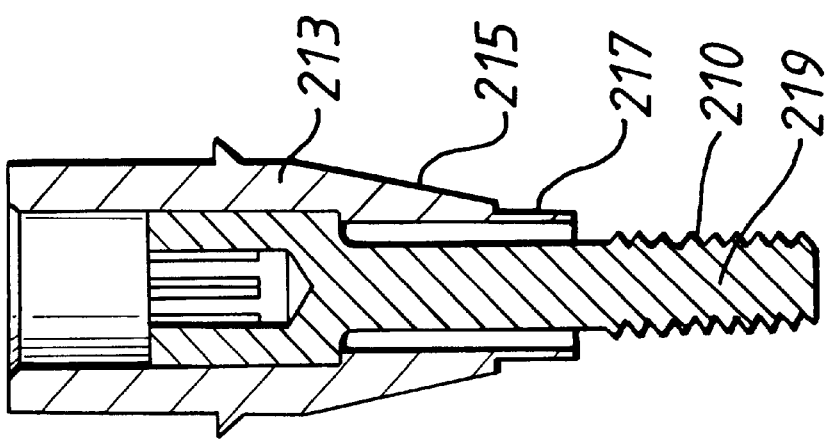

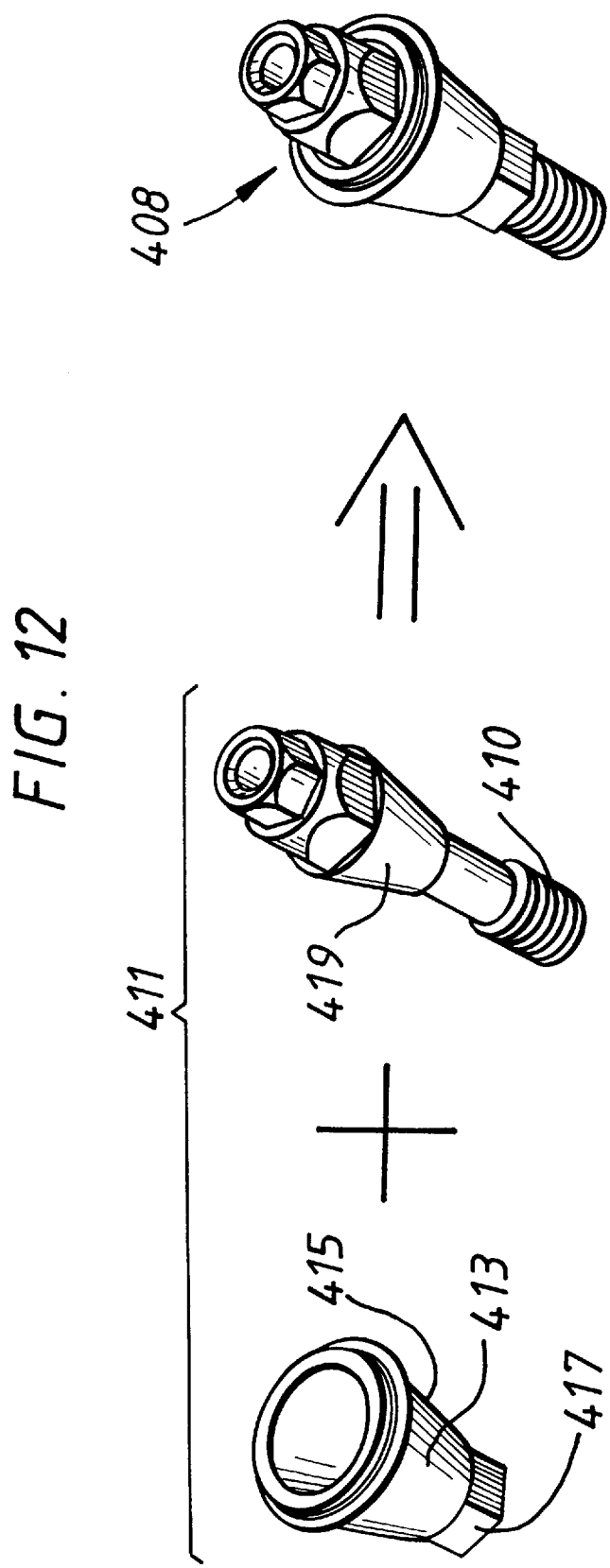

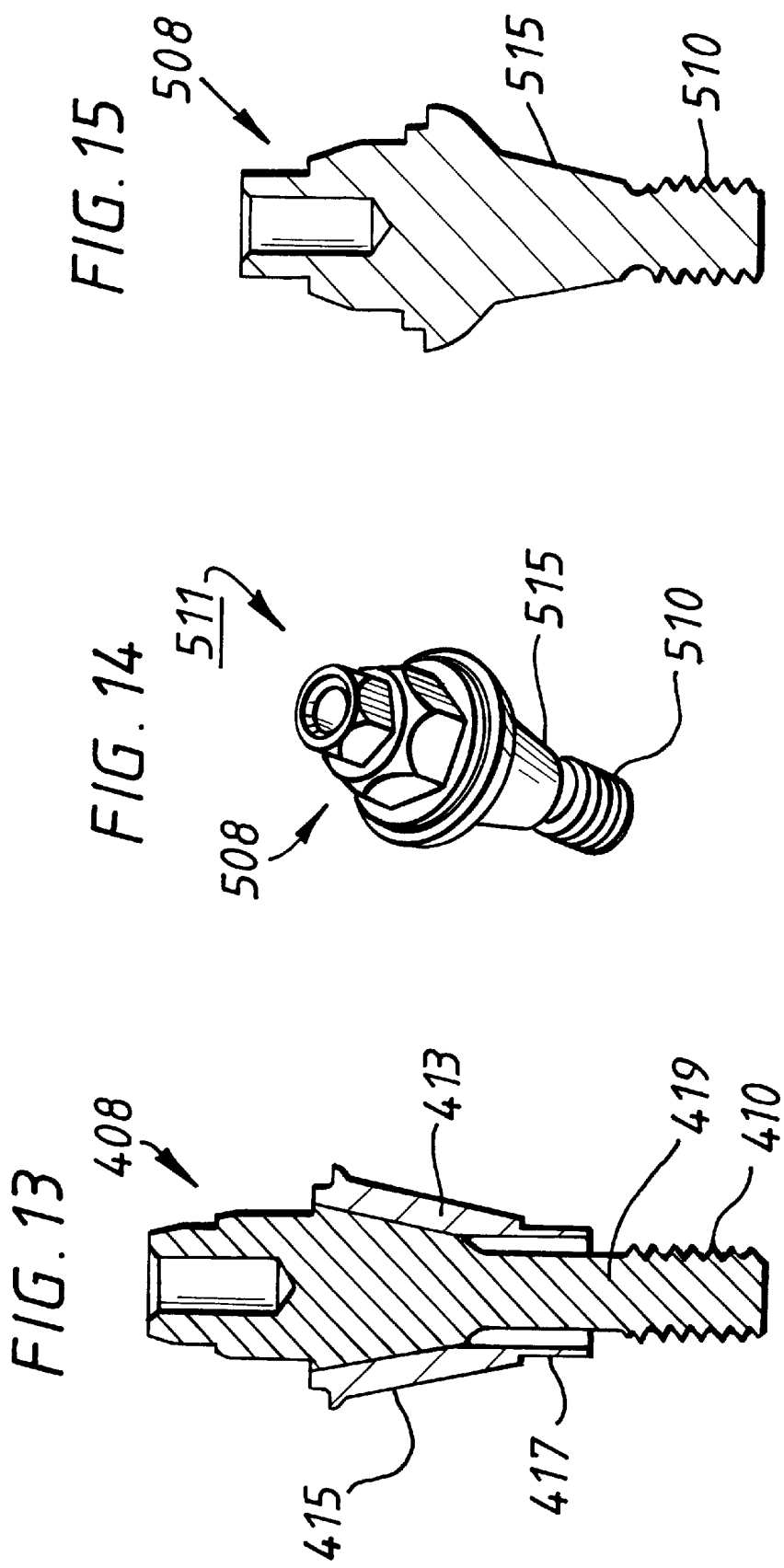

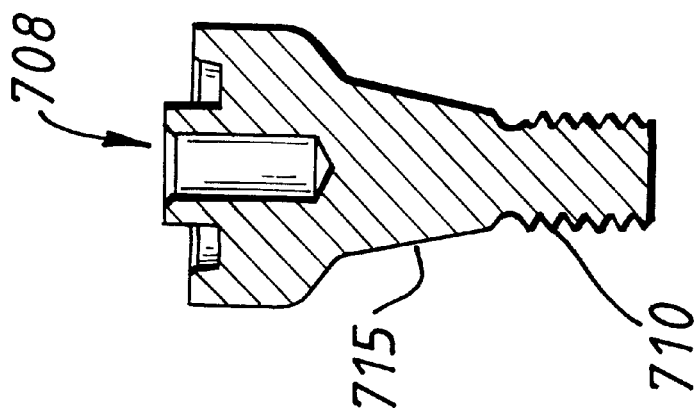
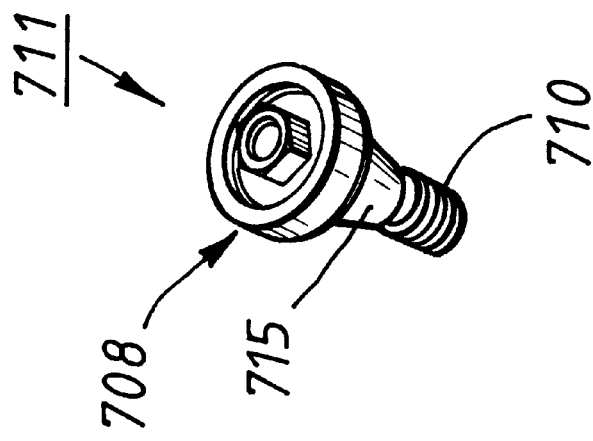
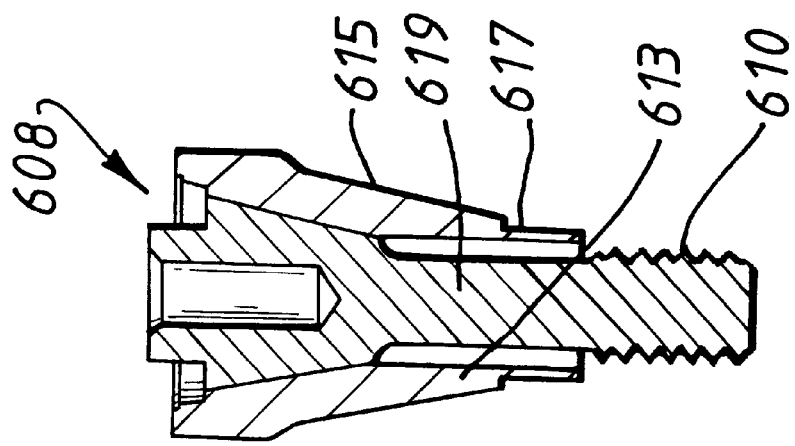

DENTAL IMPLANT SYSTEMS

FIELD OF THE INVENTION

The present invention relates to dental implant systems.

BACKGROUND OF THE INVENTION

There are many dental implant systems being marketed today by different manufacturers. The components of these systems are typically incompatible with one another meaning that a "mix-and-match" dental prosthesis is not possible. Clearly there would be many advantages to having the facility to build a dental prosthesis from components of different systems. For example, some systems include components which no other system has an equivalent to, that is to say they are unique, while some systems may have components with advantageous properties compared to the equivalent components of other systems.

The most widespread dental implant system at the present time is that marketed by Nobelpharma AB and known as the Brånemark System®. This system includes a fixture as a component part thereof which is adapted in use to be embedded in the bone tissue of the maxilla or mandible and which presents at the trailing end thereof a male hexagonal projection in which an internally threaded bore opens centrally. A variety of other components of the Brånemark System® are then added temporarily or permanently to the trailing end of the fixture Component to form a dental prosthesis.

For example, the Brånemark System® includes various transmucosal spacers or abutments as component parts for connection to an implanted fixture to bridge the soft tissue layer or gingiva overlying the maxilla or mandible and carry supragingival components of the Brånemark System®. One such abutment includes a sleeve part one of the open ends of which has an inner circumference of hexagonal cross-section for anti-rotational connection of the abutment sleeve to the trailing end of the fixture. An abutment screw then passes through the abutment sleeve to screw into the internally threaded bore in the trailing end of the fixture to secure the abutment sleeve to the fixture.

The trailing end of the abutment presents a profile such that supragingival components of the Brånemark System® can be added temporarily or permanently on the fixture-abutment assembly to complete the formation of a dental prosthesis. For example, in the case of the abutment assembly described hereinabove an internally threaded bore may open in the trailing end of the abutment screw for either a screw threaded projection on a supragingival component to screw into to secure that component to the fixture-abutment assembly or a screw part of a multi-part supragingival assembly to screw into to secure the supragingival assembly to the fixture-abutment assembly.

Abutments may also present anti-rotational surfaces for co-operation with anti-rotational surfaces on the leading end of supragingival components or assemblies for anti-rotational connection of the supragingival components or assemblies to the fixture-abutment assembly or wrench engaging surfaces which enable tightening of the abutment to the fixture but which do not interfere with the connection of the supragingival components or assemblies to the fixture-abutment assembly.

As examples of supragingival components there may be mentioned cylinders which carry a restoration such as a bridge or crown and impression copings which are temporarily connected to the implanted fixture-abutment assembly to enable a model of the implanted fixture-abutment assembly and surrounding dentition to be generated for fabrication of a restoration on a cylinder which will fit in with the surrounding dentition when carried by the fixture-abutment assembly.

In addition to the dental implant systems such as the Brånemark System® which are based on fixtures having male projections at the trailing ends thereof there also exist dental implant systems which rely on a conical seat interface between the fixtures and superstructures carried thereby. In these systems a frusto-conical recess opens in the trailing end of the fixture for a complementary frusto-conical profile at the leading end of the superstructure, for example an abutment, to seat in. The frusto-conical recess typically forms the trailing portion of a socket which at the leading end thereof defines an internally threaded bore. The superstructure is secured to the fixture through a screw connection in the internally threaded bore.

One such system is marketed by Astra Tech AB information about which can be found in inter alia '*Dental Implants: A Guide for the General Practitioner*'. Michael Norton, Ouintessence Publishing Co. Ltd., 1995. To prevent rotation of an abutment of this system of the type comprising an abutment sleeve and abutment screw, the socket in the fixture may further comprise a polygonal cross-section portion between the frusto-conical and internally threaded portions with the abutment sleeve being provided with a projection at the leading end thereof having a trailing frusto-conical portion for seating in the frusto-conical portion of the fixture socket and a leading polygonal portion for co-operation with the polygonal portion of the fixture socket. The abutment screw passes through the sleeve into engagement with the internally threaded bore to secure the sleeve to the fixture as for the corresponding abutment of the Brånemark System®.

Tests have shown that a tapered seat interface such as the conical seat interface for a fixture-superstructure assembly, for example a fixture-abutment assembly, leads to an implanted assembly which exhibits greater mechanical stability and strength as compared to the fixtures of the other systems discussed hereinabove.

In addition, the fixture of the Astra Tech system has a unique outer surface characteristic which improves the shear strength of the fixture when implanted and also the ability of the fixture to osseointegrate into the bone tissue of tho maxilla or mandible into which it is implanted.

There is thus a need for the provision of means to enable a fixture of a first dental implant system having a trailing end in which a tapered, for example frusto-conical, recess is provided to support components of a second incompatible dental implant system for the formation of a hybrid dental prosthesis founded on the fixture with the recess.

SUMMARY OF THE INVENTION

With this need in mind, the present invention provides a dental implant system converter structure for enabling a fixture of a first dental implant system having a trailing end in which a tapered recess opens to support components of a second incompatible dental implant system, the converter structure having a leading end which presents a projection having a tapered profile for seating in the tapered recess in the trailing end of the fixture and a trailing end which presents a profile adapted to enable one or more components of the second dental implant system to be carried thereon.

In an embodiment of the invention he tapered recess forms a trailing portion of a socket in the trailing end of the fixture with a leading portion of the socket presenting an internally threaded bore and the tapered profile forms a trailing portion of the projection at the leading end of the converter structure with a leading portion of the projection presenting a screw threaded profile for screw connection in the internally threaded bore portion of the fixture socket.

In an embodiment of the invention the converter structure comprises a sleeve element having a leading end which presents a first part of the projection which comprises the tapered profile and a screw element having a leading end which presents a second part of the projection which comprises the screw thread profile, the screw element adapted to be inserted into the sleeve element for the screw thread profile to be screwed in the internally threaded bore portion of the fixture socket to secure the sleeve element to the fixture. The, converter structure may, on the other hand, be a one-piece component with the projection being formed at the leading end of the component.

In an embodiment of the invention the converter structure comprises anti-rotation means for co-operation with anti-rotation means on the fixture when the tapered profile of the converter structure seats in the tapered recess in the fixture to prevent rotation of the converter structure about the axis thereof relative to the fixture. For example, the anti-rotation means may be the faces of a polygonal profile such as a hexagon presented by the projection for co-operation with the faces of a polygonal cross-section portion in the fixture socket.

When the projection is formed in part on a sleeve element and in part by a screw element as outlined hereinabove, it is convenient for the polygonal profile to be formed as a leading portion of the first part of the projection on the sleeve element with the tapered profile forming a trailing portion of the first part of the projection and the polygonal cross-section portion to be formed in the fixture socket on the leading side of the tapered recess portion, for example between the internally threaded bore portion and the tapered recess portion.

In an embodiment of the invention the converter structure is adapted to convert the trailing end presented by the fixture of the first dental implant system into the trailing end of a fixture of the second dental implant system. This has the advantage that the dental prosthesis can include the abutment of the second dental implant system as well as the supragingival components thereof when the fixture of the first system is one whose trailing end does not bridge the soft tissue layer overlying the maxilla or mandible when implanted. As an example, the trailing end presented by the converter structure may correspond to the trailing end of a fixture of the Brånemark System®.

In an alternative embodiment of the invention the converter structure takes the form of an abutment structure having a trailing end profile which allows supragingival components of the second dental implant system to be carried thereon. As an example, the sleeve element of the converter structure may be in the form of an abutment sleeve and the screw element in the form of an abutment screw.

In an embodiment of the invention the trailing end of the converter structure presents an anti-rotation profile for co-operation with a complementary anti-rotation profile presented by the leading end of a component of the second dental implant system. For example, where the fixture of the first system is one whose trailing end does not bridge the soft tissue layer overlying the maxilla or mandible when implanted and the converter structure is such as to convert the fixture of the first dental implant system to a corresponding fixture of the second dental implant system, the anti-rotation profile presented by the trailing end of the converter structure may be a male polygonal projection for anti-rotational interfacial engagement with a complementary female polygonal socket in the leading end of an abutment of the second dental implant system.

In a preferred embodiment of the invention the tapered recess which opens in the trailing end of the fixture and the tapered profile presented by the converter structure are respectively a frusto-conical recess and a complementary frusto-conical profile.

According to the invention there is further provided a dental prosthesis including a dental implant system converter structure in accordance with the invention.

According to the invention there is yet further provided a dental implant system including a dental implant system converter structure according to the invention.

According to the invention there is additionally provided the use of a dental implant system converter structure in accordance with the invention in the formation of a hybrid dental prosthesis comprising the fixture of the first dental implant system and a superstructure from the second dental implant system.

According to the invention there is also provided a method of treating toothlessness in a maxilla or mandible of a patient comprising the steps of implanting in the maxilla or mandible a fixture of a first dental implant system, mounting on the fixture a dental implant system converter structure according to the invention and mounting on the converter structure a superstructure formed from one or more components of a second incompatible dental implant system which supports or presents one or more artificial teeth.

BRIEF DESCRIPTION OF THE DRAWINGS

By way of example embodiments of the invention will now be described with reference to the accompanying Figures of drawings in which:

FIG. 3 is a perspective view of the component parts of a first dental implant system converter structure in accordance with the invention in both the unassembled and assembled state, the converter structure adapted to convert the fixture of FIGS. 1 and 2 into a standard fixture of the Brånemark System®, FIG. 4 is a side cross-sectional view of the first converter structure in the assembled state, FIG. 5 is a side cross-sectional view of an abutment of the Brånemark System®, FIG. 6 is a perspective view of a second dental implant system converter structure in accordance with the invention adapted to convert the fixture of FIGS. 1 and 2 into a standard fixture of the Brånemark System®, FIG. 7 is side cross-sectional view of the second dental implant system converter structure, FIG. 8 is a perspective view of the component parts of a third dental implant system converter structure in accordance with the invention in both the unassembled and assembled state, the converter structure having the form of a first abutment of the Brånemark System®, FIG. 9 is a side cross-sectional view of the third converter structure in the assembled state, FIG. 10 is a perspective view of a fourth dental implant system converter structure in accordance with the invention in the form of the first abutment of the Brånenark System®, Fig, 11 is a side cross-sectional view of the fourth converter structure, FIG. 12 is a perspective view of the component parts of a fifth dental implant system converter structure in accordance with the invention in both the unassembled and assembled state, the converter structure having the form of a second abutment of the Brånemark System®, FIG. 13 is a side cross-sectional view of the fifth converter structure in the assembled state, FIG. 14 is a perspective view of a sixth dental implant system converter structure in accordance with the invention having the form of the second abutment of the Brånemark System®, FIG. 15 is a side cross-sectional view of the sixth converter structure, FIG. 17 is a side cross-sectional view of the seventh converter structure in the assembled state, FIG. 18 is a perspective view of an eighth dental implant system converter structure in accordance with the invention having the form of the abutment of the Brånemark System® shown in FIG. 5, and FIG. 19 is a side cross-sectional view of the eighth converter structure.

DESCRIPTION OF EXEMPLARY EMBODIMENTS OF THE INVENTION

Figure 1:
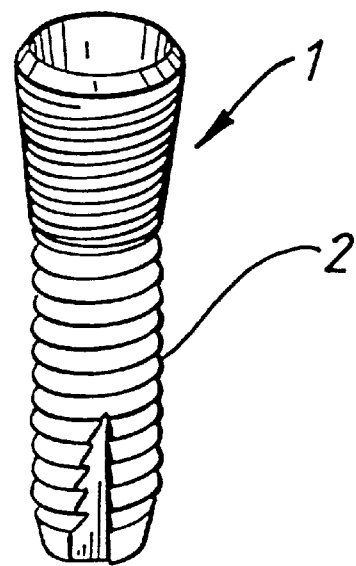
FIG. 1 is a view of a fixture from the system marketed by Astra Tech AB.
Figure 2:
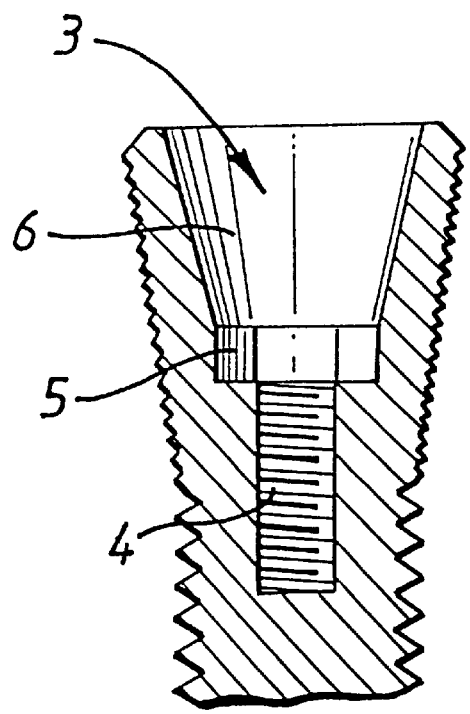
FIG. 2 is a side cross-sectional view of the trailing end of the fixture of FIG. 1.

FIGS. 1 and 2 show a standard fixture 1 of the Astra Tech AB system. The fixture 1 has a screw threaded outer surface profile 2 which to advantage may also be pitted by blasting thereof with particles of a titanium oxide as outlined in U.S. Pat. No. 5,484,286. In the trailing end of the fixture 1 there opens a socket 3 comprising three different portions, namely (i) an internally threaded bore portion 4, (ii) a hexagonal portion 5, and (iii) a frustoconical portion 6.

Turning now to FIGS. 3 and 4, there is shown a two-piece converter structure 11 for connection to the trailing end of the fixture 1 of FIGS. 1 and 2 to convert the trailing end of the fixture 1 to the trailing end of a fixture of the Brånemark System®. The converter structure 11 comprises a sleeve 13 having an outer profile which includes frusto-conical and hexagonal portions 15, 17 for respective interfacial engagement with the frusto-conical and hexagonal portions 6, 5 of the fixture socket 3. The converter structure 11 further comprises a screw 19 having a screw threaded leading end 10 for interlocking of the converter structure 11 to the fixture 1 by passage thereof through the sleeve 13 into the internally threaded bore portion 4 of the fixture socket 3.

The trailing ends of the sleeve 13 and screw 19 collectively present a profile which corresponds to the trailing end profile of a fixture of the Brånemark System®, for example a hexagonal projection 18 in which an internally threaded bore 20 opens. An abutment of the Brånemark System® such as the abutment 21 shown in FIG. 5 is thus able to be carried by the fixture 1, the abutment 21 in turn being able to carry supragingival components of the Brånemark System®.

The abutment 21 comprises a sleeve 23 having an axial bore therethrough which terminates in a hexagonal leading end opening 25 for anti-rotational interfacial engagement with the hexagonal projection 18 presented by the converter structure 11. The abutment further comprises an abutment screw 27 which screws into the internally threaded bore 20 presented in the trailing end of the converter structure 11 to secure the abutment 21 to the converted fixture.

In FIGS. 6 and 7 there is shown an alternative converter structure 111 for providing the fixture 1 of FIGS. 1 and 2 with the same trailing end as the converter structure 11 hereinabove described with reference to FIGS. 3 and 4. In this case, though, the converter structure 111 is a one-piece structure. For this reason, the converter structure 111 is not provided with a hexagonal cross-section portion for interfacial engagement with the hexagonal portion 5 of the fixture socket 3. In common with the converter structure 11, however, the converter structure 111 presents a screw thread profile portion 110 for screwing into the internally threaded portion 4 of the fixture socket 3, a frusto-conical portion 115 for seating in the frusto-conical portion 6 of the fixture socket 3 and a trailing end profile 108 on which the abutment 21 of the Brånemark System® can secure to.

In FIGS. 8 and 9 there is shown a two-piece converter structure 211 for attachment to the fixture 1 shown in FIGS. 1 and 2 which functions as an abutment. The converter structure 211 comprises a sleeve 213 having an outer profile which includes frusto-conical and hexagonal portions 215, 217 for respective interfacial engagement with the frusto-conical and hexagonal portions 6, 5 of the fixture socket 3. The converter structure 211 further comprises a screw 219 having a screw threaded leading end 210 for interlocking of the converter structure 211 to the fixture 1 by passage thereof through the sleeve 213 into the internally threaded bore portion 4 of the fixture socket 3, the screw 219 having a socket 214 in the trailing end thereof for a screw driver or the like to engage in to screw the screw 219 into the internally threaded bore 4.

The trailing ends of the sleeve 213 and screw 219 collectively present a profile 208 which corresponds to the trailing end profile of an abutment of the Brånemark System® (called "CERAONE"). The converter structure 211 thus allows the fixture 1 to carry supragingival components of the Brånemark System®.

In FIGS. 10 and 11 there is shown a one-piece converter structure 311 which achieves the same result as the two-piece converter structure 211 of FIGS. 8 and 9. The one-piece converter structure 311 has a leading end outer surface profile having screw threaded and frusto-conical portions 310, 315 to enable the converter structure 311 to be secured in the socket 3 of the fixture 1 and a trailing end profile 310 corresponding to the CERAONE abutment of the Brånemark System®. The main difference between the one-piece converter structure 311 and the two-piece equivalent is that no hexagonal cross-section portion is provided for anti-rotational interfacial engagement in the hexagonal portion 5 of the socket 3 in the fixture 1.

In FIGS. 12 and 13 there is shown another two-piece converter structure 411 for attachment to the trailing end of the fixture 1 shown in FIGS. 1 and 2 which functions as an abutment. The converter structure 411 comprises a sleeve 413 having an outer profile which includes frusto-conical and hexagonal portions 415, 417 for respective interfacial engagement with the frusto-conical and hexagonal portions 6, 5 of the fixture socket 3. The converter structure 411 further comprises a screw 419 having a screw threaded leading end 410 for interlocking of the converter structure 411 to the fixture 1 by passage thereof through the sleeve 413 into the internally threaded bore portion 4 of the fixture socket 3.

The trailing ends of the sleeve 413 and screw 419 collectively present a profile 408 which corresponds to the trailing end profile of another abutment of the Brånemark System® (called "ESTHETICONE"). The converter structure 411 thus also allows the fixture 1 to carry supragingival components of the Brånemark System®.

In FIGS. 14 and 15 there is shown a one-piece converter structure 511 which achieves the same result as the two-piece converter structure 411 of FIGS. 12 and 13. The one-piece converter structure 511 has a leading end outer surface profile having screw threaded and frusto-conical portions 510, 515 to enable the converter Structure 511 to be secured in the socket 3 of the fixture 1 and a trailing end profile 508 corresponding to the ESTHETICONE abutment of the Brånemark System®. The main difference between the one-piece converter structure 511 and the two-piece equivalent is that again no hexagonal cross-section portion is provided for anti-rotational interfacial engagement in the hexagonal portion 5 of the socket 3 in the fixture 1.

Figure 16:
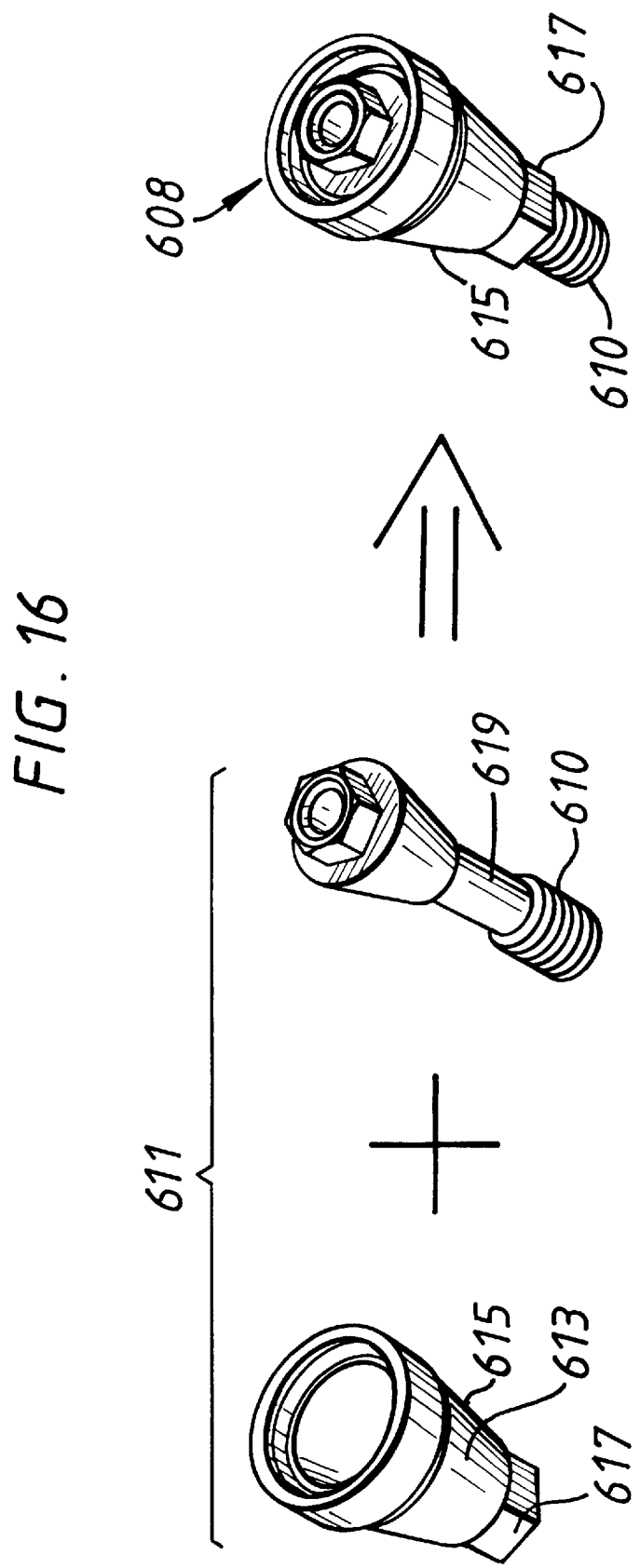
FIG. 16 is a perspective view of the component parts of a seventh dental implant system converter structure in accordance with the invention in both the unassembled and assembled state, the converter structure having the form of the abutment of the Brånemark. System® shown in FIG. 5.

In FIGS. 16 and 17 there is shown a yet further two-piece converter structure 611 for attachment to the fixture 1 shown in FIGS. 1 and 2 which functions as an abutment. The converter structure 611 comprises a sleeve 613 having an outer profile which includes frusto-conical and hexagonal portions 615, 617 for respective interfacial engagement with the frusto-conical and hexagonal portions 6, 5 of the fixture socket 3. The converter structure 611 further comprises a screw 619 having a screw threaded leading end 610 for interlocking of the converter structure 611 to the fixture 1 by passage thereof trough the sleeve 613 into the internally threaded bore portion 4 of the fixture socket 3.

The trailing ends of the sleeve 613 and screw 619 collectively present a profile 608 which corresponds to the trailing end profile of the abutment of the Brånemark System® shown in FIG. 5 (called "Standard"). The converter structure 611 thus also allows the fixture 1 to carry supragingival components of the Brånemark System®.

In FIGS. 18 and 19 there is shown a one-piece converter structure 711 which achieves the same result as the two-piece converter structure 611 of FIGS. 16 and 17. The one-piece converter structure 711 has a leading end outer surface profile having screw threaded and frusto-conical portions 710, 715 to enable the converter structure 711 to be secured in the socket 3 of this fixture 1 and a trailing end profile 708 corresponding to the Standard abutment of the Brånemark System®. Once again, the main difference between the one-piece converter structure 711 and the two-piece equivalent is that no hexagonal cross-section portion is provided for anti-rotational interfacial engagement in the hexagonal portion 5 of the socket 3 in the fixture 1.

The converter structures described hereinabove with reference to the accompanying Figures of drawings are given for the purposes of illustration only. Readers skilled in the art will readily appreciate that other constructions could be adopted to convert the fixture of the Astra Tech AB system to accepting higher order components of the Brånemark System®.

Although the invention has been described with reference to conversion of a fixture of the Astra Tech AB system to carry a superstructure from the Brånemark System® it is to be understood that the invention is not limited solely to use with these two incompatible systems. The invention is for enabling a fixture of a dental implant system having a trailing end in which a tapered recess opens to carry components from another incompatible dental implant system.

What is claimed is:

1. A system for providing a hybrid dental implant, comprising in combination:
   a fixture of a first dental implant system, said fixture having a tapered recess which opens in a trailing end of the fixture;
   at least one component of a second dental implant system that is incompatible with the first system in the sense that said component has a profile which is adapted to fit with a fixture of the second system but which is incompatible with said tapered recess of said fixture of the first system; and
   a dental implant system converter structure, which is adapted to enable said fixture of the first system to support components of the second system, said converter structure having:
   a leading end which presents a projection having a tapered profile which matches and is adapted to be seated in said tapered recess of the fixture of the first system, and
   a trailing end which presents a profile adapted to enable one or more components of the second system to be supported thereon.

2. The system as claimed in claim 1, wherein the tapered recess forms a trailing portion of a socket in the trailing end of the fixture with a leading portion of the socket presenting an internally threaded bore and the tapered profile forms a trailing portion of the projection at the leading end of the converter structure with a leading portion of the projection presenting a screw threaded profile for screw connection in the internally threaded bore portion of the fixture socket.

3. The system as claimed in claim 2, wherein the converter structure comprises a sleeve element having a leading end which presents a first part of the projection which comprises the tapered profile and a screw element having a leading end which presents a second part of the projection which comprises the screw thread profile, the screw element adapted to be inserted into the sleeve element for the screw thread profile to be screwed in the internally threaded bore portion of the fixture socket to secure the sleeve element to the fixture.

4. The system as claimed in claim 3, wherein the converter structure comprises anti-rotation means for co-operation with anti-rotation means on the fixture when the tapered profile of the converter structure seats in the tapered recess in the fixture to prevent rotation of the converter structure about the axis thereof relative to the fixture.

5. The system as claimed in claim 4, wherein the anti-rotation means are the faces of a polygonal profile presented by the projection for co-operation with the faces of a polygonal cross-section portion in the fixture socket.

6. The system as claimed in claim 5, wherein the polygonal profile is formed as a leading portion of the first part of the projection with the tapered profile forming a trailing portion of the first part of the projection.

7. The system as claimed in claim 6, wherein the polygonal cross-section portion of the fixture socket is disposed between the internally threaded bore-portion and the tapered recess.

8. The system as claimed in claim 5, wherein the polygonal cross-section portion of the fixture socket is disposed between the internally threaded bore-portion and the tapered recess.

9. The system as claimed in claim 2, wherein the converter structure comprises anti-rotation means for co-operation with anti-rotation means on the fixture when the tapered profile of the converter structure seats in the tapered recess in the fixture to prevent rotation of the converter structure about the axis thereof relative to the fixture.

10. The system as claimed in claim 9, wherein the anti-rotation means are the faces of a polygonal profile presented by the projection for co-operation with the faces of a polygonal cross-section portion in the fixture socket.

11. The system as claimed in claim 10, wherein the polygonal cross-section portion of the fixture socket is disposed between the internally threaded bore-portion and the tapered recess.

12. The system as claimed in claim 1, wherein the converter structure comprises anti-rotation means for co-operation with anti-rotation means on the fixture when the tapered profile of the converter structure seats in the tapered recess in the fixture to prevent rotation of the converter structure about the axis thereof relative to the fixture.

13. The system as claimed in any one of claims 1, 2 or 12, wherein the converter structure takes the form of an abutment structure having a trailing end profile which allows supragingival components of the second dental implant system to be carried thereon.

14. The system as claimed in any one of claims 1, 2, 3, and 12, wherein the trailing end of the converter structure presents an anti-rotation profile for co-operation with a complementary anti-rotation profile presented by the leading end of a component of the second dental implant system.

15. The system as claimed in any one of claims 1, 2, 3, and 12, wherein the tapered recess which opens in the trailing end of the fixture and the tapered profile presented by the converter structure are respectively a frusto-conical recess and a complementary frusto-conical profile.

16. A method of treating toothlessness in the maxilla or mandible of a patient using the system for providing a hybrid dental implant as claimed in any one of claims 1, 2, 3, and 12, comprising the steps of:
    implanting in the mandible or the maxilla a fixture of a first dental implant system;
    mounting on the fixture a dental implant system converter structure; and
    mounting on the converter structure a superstructure formed from one or more components of a second incompatible dental implant system which supports or presents one or more artificial teeth.

17. The system as claimed in claim 3 or 6, wherein the converter structure takes the form of an abutment structure having a trailing end profile which allows supragingival components of the second dental implant system to be carried thereon.

18. The system as claimed in claim 17, wherein the sleeve element of the converter structure is in the form of an abutment sleeve and the screw element is in the form of an abutment screw.

19. The system as claimed in any one of claims 5, 7, 8, 10 and 11, wherein the polygonal profile is a hexagon.

20. A system for providing a hybrid dental implant, comprising in combination:
    a first component of a first dental implant system, said first component having a trailing end;
    at least one component of a second dental implant system that is incompatible with the first system in the sense that said component of the second system has a profile which is adapted, to fit with a secondary component of the second system but which is incompatible with said first component of the first system; and
    a dental implant converter structure, which is adapted to enable said first component of the first system to support said at least one component of the second dental implant system, said converter structure having:
        a leading end which is adapted to be seated in the trailing end of said first component of the first dental implant system, and
        a trailing end which presents a profile adapted to enable one or more components of the second dental implant system to be supported thereon.

21. The system as claimed in claim 20, wherein the first component is a dental implant fixture.

22. The system as claimed in claim 20, wherein the first component is an abutment.

23. The system as claimed in claim 20 or 21, wherein the second component is an abutment.

24. The system as claimed in claim 20 or 21, wherein the converter structure is in the form of an abutment which allows at least one supragingival component of the second dental implant system to be carried thereon.

25. The system as claimed in claim 20 or 21, wherein the converter structure comprises anti-rotation means for co-operation with anti-rotation means of a component selected from the group consisting of the first component and the second component.

26. The system as claimed in claim 20 or 22, wherein the second component is supragingival.

27. The system as claimed in claim 26, wherein the second component comprises at least one artificial tooth.

28. The system as claimed in claim 26, wherein the second component supports at least one artificial tooth.

29. A system for providing a hybrid dental implant, comprising in combination:
    a first component of a first dental implant system, said first component having a trailing end;
    at least one secondary component of a second dental implant system that is incompatible with the first system in the sense that said secondary component has a leading end which is adapted to fit with a trailing end of a first component of the second system but which is incompatible with said trailing end of the first component; and
    a dental implant system converter structure, which is adapted to enable said first component of the first system to support said secondary component of the second dental implant system, said converter structure having:
        a leading end which is adapted to be seated in the trailing end of said first component of the first system, and
        a trailing end which presents a profile that is so adapted to the leading end of said secondary component of the second system, that the profile enables said secondary component of the second dental implant system to be supported on the trailing end of the converter structure.

30. The system as claimed in claim 29, wherein the first component is a dental implant fixture.

31. The system as claimed in claim 29, wherein the first component is an abutment.

32. The system as claimed in claim 29 or 30, wherein the second component is an abutment.

33. The system as claimed in claim 29 or 30, wherein the converter structure is in the form of an abutment which allows at least one supragingival component of the second dental implant system to be carried thereon.

34. The system as claimed in claim 29 or 30, wherein the converter structure comprises anti-rotation means for co-operation with anti-rotation means of a component selected from the group consisting of the first component and the second component.

35. The system as claimed in claim 29 or 31, wherein the second component is supragingival.

36. The system as claimed in claim 35, wherein the second component comprises at least one artificial tooth.

37. The system as claimed in claim 35, wherein the second component supports at least one artificial tooth.

* * * * *

UNITED STATES PATENT AND TRADEMARK OFFICE
CERTIFICATE OF CORRECTION

PATENT NO. : 6,358,050 B1  
DATED : March 19, 2002  
INVENTOR(S) : Bergström et al.

It is certified that error appears in the above-identified patent and that said Letters Patent is hereby corrected as shown below:

Column 9,  
Lines 61-62, delete "claims 5, 7, 8, 10 and 11" and insert therefor -- claims 5-8, 10 and 11 --.

Signed and Sealed this

Fifteenth Day of October, 2002

*Attest:*

*Attesting Officer*

JAMES E. ROGAN  
*Director of the United States Patent and Trademark Office*